(12) United States Patent  
Simon et al.

(10) Patent No.: US 6,616,670 B2
(45) Date of Patent: Sep. 9, 2003

(54) BONE NAIL TARGETING SYSTEM

(75) Inventors: Bernd Simon, Kiel (DE); René Füllgraf, Kiel (DE)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 09/949,904

(22) Filed: Sep. 10, 2001

(65) Prior Publication Data

US 2002/0052604 A1 May 2, 2002

(30) Foreign Application Priority Data

Sep. 12, 2000 (DE) .................................. 200 15 775 U

(51) Int. Cl.⁷ ............................................... A61B 17/72
(52) U.S. Cl. ........................................... 606/62; 606/72
(58) Field of Search ............................. 606/53, 60, 62, 606/64, 67, 86, 96, 1, 72

(56) References Cited

U.S. PATENT DOCUMENTS

| 4,621,628 A | | 11/1986 | Brudermann | |
|---|---|---|---|---|
| 5,127,913 A | * | 7/1992 | Thomas, Jr. | 606/62 |
| 5,411,503 A | | 5/1995 | Hollstien et al. | |
| 5,540,691 A | * | 7/1996 | Elstrom et al. | 606/64 |
| 5,584,838 A | | 12/1996 | Rona et al. | |
| 5,993,456 A | | 11/1999 | Speitling et al. | |
| 6,503,249 B1 | * | 1/2003 | Krause | 606/62 |

FOREIGN PATENT DOCUMENTS

| EP | 0589592 | * | 3/1994 | ............ A61B/17/56 |
|---|---|---|---|---|
| WO | WO97/26826 | * | 1/1996 | ............ A61B/8/00 |
| WO | WO 97/13467 | | 4/1997 | |

* cited by examiner

Primary Examiner—Kevin Shaver
Assistant Examiner—Michael B. Priddy
(74) Attorney, Agent, or Firm—Lerner, David, Littenberg, Krumholz & Mentlik, LLP

(57) ABSTRACT

A bone nail including a hollow shank which has at least one cross-bore to receive a bone screw. A retaining sleeve is inserted into the shank to receive one or more signal generators. The signal generators received in the sleeve are adapted to emit signals at a predetermined spacing from and in a predetermined alignment relative to the cross-bore wherein the retaining sleeve has recesses or through openings in its wall to accommodate the signal generators.

25 Claims, 2 Drawing Sheets

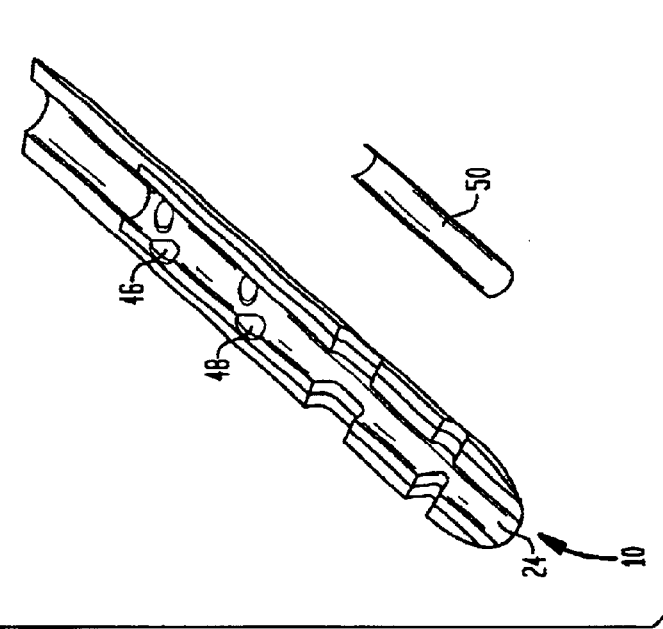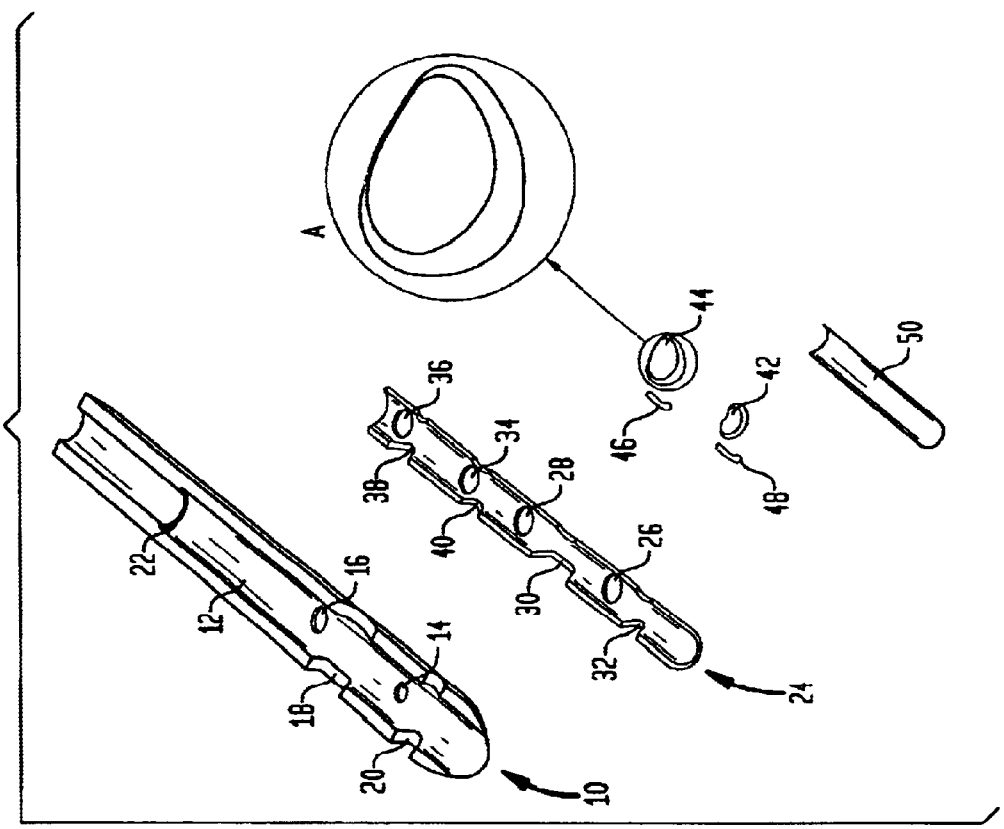

BONE NAIL TARGETING SYSTEM

BACKGROUND OF THE INVENTION

The invention relates to a bone nail having openings for receiving one or more transmitting units which emit signals at a predetermined distance from and in a predetermined alignment relative to cross-bores in the nail and to an apparatus for applying an electrical excitation signal to the transmitting units in the form of signal generators disposed in the bone nail.

It is known to use so-called locking nails to treat bone fractures in tubular bones. These nails have cross-bores through which bone screws are passed in order to retain the bone fragments on the bone nail and to secure the fragments from being displaced and distorted. Before the bone screws can be turned in it is necessary to drill holes into the cortical mass. These holes must be aligned with the cross-bores of the bone nail in a relatively precise way.

Numerous methods and apparatus have been developed to find the point where a bore for the bone screw should be placed. Most aim-taking instruments operate according to the principle of X-ray examination. The operator can determine the location of the cross-bores in the bone nail within the bone on the screen and can place the drill accordingly. However, mechanical aiming instruments are also known which can be positioned onto the free end of the bone nail. The spacing of the cross-bore from the end of the bone nail is known. The rotational position of the cross-bore can also be indicated by an appropriate marking at the end of the bone nail. Then, the cortical mass may be drilled through by means of a suitable aiming sleeve. Neither the patient nor his operator will be exposed to X-ray radiation when the mechanical aiming instrument is used in lieu of the X-ray examination process. The disadvantage of the mechanical aiming instrument is that any distortion of the nail, while being driven in, causes deviations in the location of the cross-bores which cannot be detected by the aiming instrument.

An aiming instrument for locking screws used in bone nails in medullary bones has become known from U.S. Pat. No. 5,411,503, the teachings of which are incorporated herein by reference. In this method, a pointed guide bar is introduced into the hollow bone nail. The pointed guide bar is provided with two oscillating circuits at its distal end. The pointed guide bar has a stop at its proximal end. To position an aiming instrument, the pointed guide bar is completely inserted into the bone nail which was driven in with the stop member resting on the proximal end of the nail. The two oscillating circuits at the distal end of the bar are excited and the electromagnetic field which they emit is detected by appropriate sensors on an aiming instrument. The aiming instrument is aligned in the field of the oscillating circuits in such a way that a guide channel connected thereto for the drill is aligned on the one nail according to the cross-bore. This apparatus has the disadvantage that a distortion or upsetting of the bone nail which occurs while the nail is driven in cannot be taken into account like for the previously described mechanical aiming instruments.

From U.S. Pat. No. 5,584,838, the teachings of which are incorporated herein by reference, a bone nail is shown having a hollow shank into which a member having a single oscillating circuit is inserted. The nail is driven into the bone with the member inserted so that the aforementioned disadvantages of the nail getting distorted cannot occur. However, a nail formed in such a way requires a comparatively expensive aiming instrument to align the drill since only a single oscillating circuit is used in the nail. What further proves to be a disadvantage is that the oscillating circuit must be disposed accurately in the channel of the cross-bore in order that the location of the cross-bore may be precisely detected. The member which was inserted is removed again after the channel of the cross-bore is detected.

SUMMARY OF THE INVENTION

It is the object of the invention to provide a bone nail wherein the location of its cross-bores can reliably be determined by simple means after it is driven in.

According to the invention, the bone nail has a hollow shank which is provided with at least one cross-bore to receive a bone screw and the like. In the area of the cross-bore, the shank is fitted with a retaining device for at least one signal generator which is adapted to emit signals at a predetermined spacing from and in a predetermined alignment relative to the cross-bore. The signals can be detected by means of an aim-taking instrument which is introduced by the operator outside the nail. The position in an axial direction and the alignment of the cross-bore can be determined with reference to the position and orientation of the radiation emitted. The signal generator can be provided as a passive or active component. In a preferred embodiment the signal generator is a passive oscillating circuit. Also a transponder can be provided as a passive component. The signal generator generates and emits a signal in response to an electrical excitation signal. The excitation signal is applied to the signal generator by means of a guide bar with an electrical conductive tip. The emitted signal is detected from the outside of the bone by the aiming instrument.

The retaining device has an insert disposed in the shank. Preferably, the insert is in a sleeve-like fashion and, on its inner wall, is provided with recesses or through openings to receive one signal generator for each retaining device each. The insert is aligned in the shank of the bone nail, which allows for determining the bore location after the nail is driven in. Since at least two signal generators are preferably used in the insert the aiming instruments used are of a comparatively simple structure. The signal generators need not be disposed in a flush relationship with the cross-bore, but may be disposed and aligned at spacings in the shank. Because a sleeve-shaped insert having a through passage is preferably used and the signal generators are disposed in the insert wall a free through passage will remain in the shank and, for example, will permit the driving in of the bone nail along a pointed guide bar. In the inventive bone nail, the signal generators will permanently remain in the bone nail.

In order to ensure the correct alignment of the insert in an axial direction after the nail is driven in, the shank has formed therein an inwardly projecting shoulder or protrusion on which the insert introduced into the shank bears in an axial direction. The insert finishes in a flush fashion with the inner wall of the shank so that an inner wall is formed which substantially is continuously flat. Preferably, the insert is provided at the proximal end of the insert so that this one is supported on the shoulder during the drive-in operation.

For an alignment of the insert in a radial direction, the insert is provided with bores extending transversely to the longitudinal direction and are aligned in the shaft according to the cross-bores. The bores in the insert allow the alignment of the insert in its inserted condition in the shaft according to the bores, which causes the transmitting devices in the insert to be aligned in a way dependent on the bores.

Preferably, the retaining member additionally has a sleeve-shaped contact member which covers one or more recesses or through openings for the signal generator. The contact member is connected to the signal generator in an electrically conductive way, and is electrically insulated with respect to the insert. Such a contact member increases the contact surface of the transmitting device. Preferably, the signal generator additionally connects to the wall of the bone nail as a second contact. The transmitting device introduced in the insert also is electrically insulated from the insert here. In this embodiment, a current flows across the contact element and through the signal generator and into the wall of the bone nail.

The object according to the invention is also achieved by a bone nail including a shank which preferably is hollow and has at least one cross-bore for receiving a bone screw and the like. The wall of the shank has recesses or through openings for receiving one or more signal generators and the signal generators received therein being adapted to emit signals at a predetermined spacing from and in a predetermined alignment relative to the cross-bore. In this aspect of the bone nail, an insert is unnecessary in contrast to the first embodiment described. The signal generators are disposed directly in the recesses or through openings in the wall of the shaft. The recesses may be selectively accessible from inside or outside here, which depends on the configuration of the shank in the shank wall. The transmitting devices may be appropriately retained either in the recess or the through opening, which depends on the design of the signal generator used.

To reliably localize the signals emitted by the signal generators, it is advantageous to dispose the signal generators in the insert or the shank wall in pairs each in an axial direction and in a fashion offset from each other. This forms two parallel emission characteristics which allow reliable aligning of an aiming instrument.

In a useful aspect of the invention, the signal generator concerned is a passive or active component, preferably in the shape of a tablet, which emits a transmit signal in response to excitation signals which are received or applied thereto. Preferably, the component concerned is a passive oscillating circuit. A transponder can also be provided as a component. The use of passive transmitting devices is beneficial particularly since they will remain in the bone nail and because a power supply need not be provided for them in the bone nail. The signal generator has the shape of a tablet the front-end face of which is adapted to the inside diameter and is concavely bulged.

The electrical transmission signals may be applied to the inner contact surface of the signal generator via a bar-shaped device with the bar-shaped device having an electrically insulated shank the outside diameter of which is smaller than the inside diameter of the shank in the bone nail, and being connected to an electrically conductive tip. The device permits the application of an excitation signal, which releases a transmission signal, to the signal generators by means of the electrically conductive tip. This proves to be advantageous, particularly in using oscillating circuits, because it enables the provision of excitation signals to the signal generator at a frequency which corresponds to the resonant frequency of the signal generator. Preferably, pairs of signal generators have differing resonant frequencies. If transponders are used it is also possible to send their excitation signals from inside or outside the shank.

A preferred embodiment will now be described in detail below with reference to the accompanying drawings. In the drawings:

FIG. 1 shows an exploded representation of an inventive nail tip in a longitudinal section;

FIG. 2 shows a perspective view of an assembled nail tip with an insert in a longitudinal section.

DESCRIPTION OF THE PREFERRED EMBODIMENTS

Figure 3:
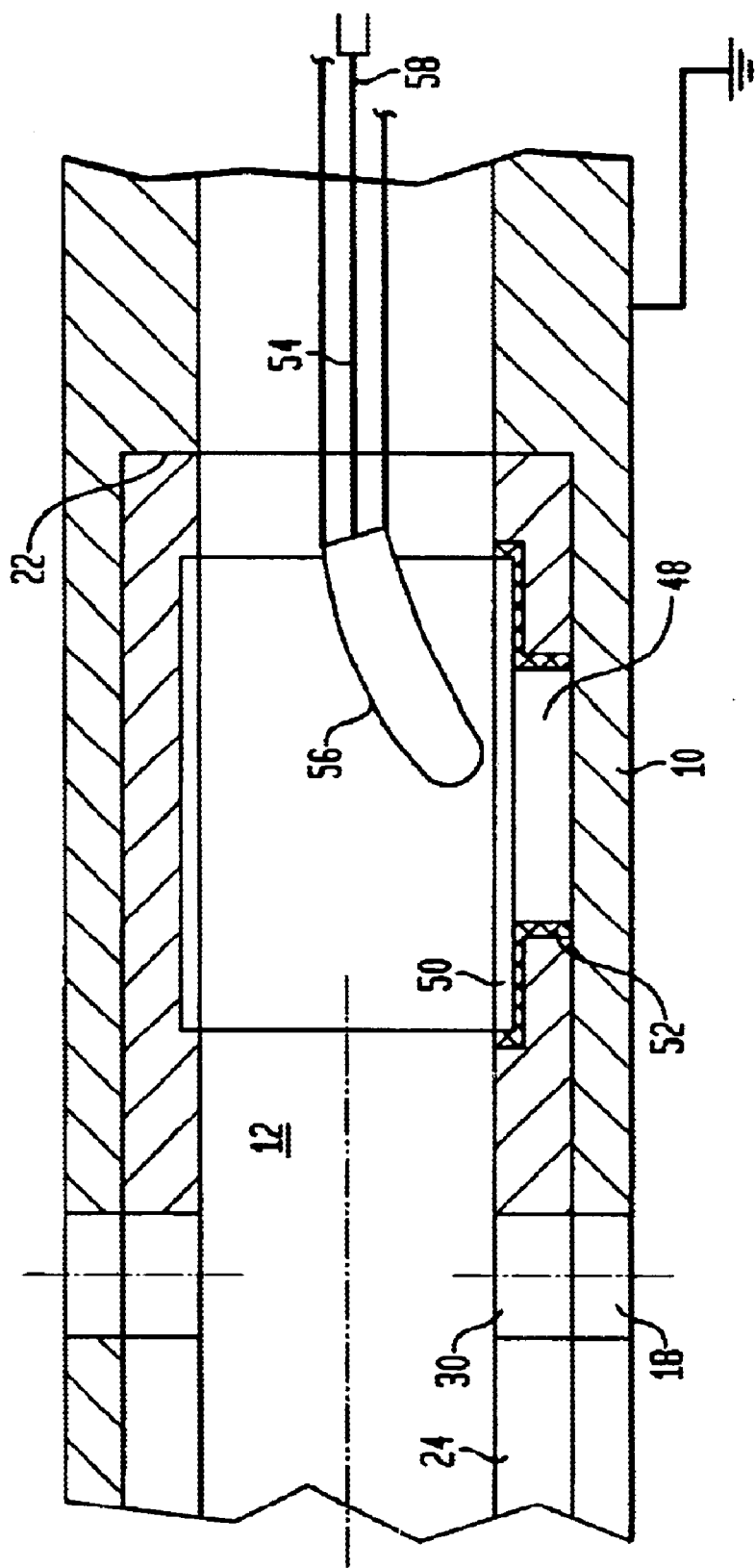
FIG. 3 shows a schematic cross-section through a nail in the area of its tip.

FIG. 1 shows the tip of a bone nail 10 in a longitudinal section. Nail 10 has a channel 12 which is circular in cross-section and is open at the distal end of nail 10. Bores 14 and 16 are provided in the wall of nail 10. The longitudinal section shown illustrates two more bores 18, 20 which are cut open and are disposed in a position offset from bores 14 and 16 in the shank. A shoulder 22 is formed in channel 12.

The insert formed as a sleeve 24 is also shown in a longitudinal section. The sleeve is hollow and has an outside diameter which corresponds to the diameter of the channel 12. Sleeve 24 has two bores 26 and 28 which match bores 14 and 16 when the sleeve is inserted. Bores 18 and 20 of the bone nail which extend transversely to bores 26 and 28 are matched by corresponding bores 30 and 32 which are provided in sleeve 24. In addition to the bores which correspond to the cross-bores of the bone nail through openings 34 and 36 are provided in the sleeve. The through openings 38 and 40 associated with the through openings 34 and 36 are cut open in the longitudinal section which is shown.

The signal generators 42 to 48 are inserted in the through openings 34 through 40. The signal generator 44 is shown enlarged in the view A. It is of a substantially circular shape with its base surfaces adapted to the bulge of channel 12 in nail 10. The thickness of the signal generator corresponds to the thickness of the sleeve adjacent to the through opening here. This configuration imparts the approximate shape of a tablet to the signal generator. The signal generators inserted are covered by the sleeve-shaped contact member 50.

FIG. 2 shows nail tip 10 with sleeve 24 inserted. The signal generators 42 to 48 are also inserted in sleeve 24 and are covered by the contact member 50. Sleeve 24 and contact member 50 bear on shoulder 22 in an axial direction of the nail.

FIG. 3 shows a cross-section through nail 10 adjacent to cross-bore 30. Nail 10 has inserted therein sleeve 24 with its bore 30. The sleeve is aligned in the nail tip such that bore 30 coincides with bore 18 of the nail's outer wall. Signal generator 48 is disposed at a spacing from bore 30 in through opening 40 of the sleeve. At its front-end faces, the signal generator 48 is in an electrical contact with the wall 10 of the nail and the contact element 50 which was inserted. Outside the contact areas, the transmitter 48 is shielded by an insulator 52 from sleeve 24.

Channel 12 of the nail has inserted therein a pointed guide bar 54 the electrically conductive tip 56 of which is connected to a signal source via an electric conductor 58. An electrical excitation signal, which causes the signal generator 48 to emit respective signals, is applied to the signal generator 48 by means of the bent tip 56. The outer wall of the nail is grounded for this purpose.

As an alternative to the embodiment shown in FIG. 3, it is also possible to excite the signal generator 48 by electromagnetic waves to emit signals as is practicable for transponders, for example. The source for exciting a transponder can also be introduced into the shank via a pointed guide bar. Alternatively, it is possible to excite the signal generators also from outside if suitable excitation frequencies are chosen for the excitation signals. The sleeve 24 with its signal generators will remain in the bone nail after the bone screws are inserted.

What is claimed is:

1. A bone nail comprising a hollow shank extending along a longitudinal axis which has at least one cross-bore to receive a bone screw, and retaining means which are inserted into the shank receiving one or more signal generators wherein the signal generators received therein are adapted to emit signals at a predetermined spacing from and in a predetermined alignment relative to the cross-bore, the retaining means have an insert which has at least one opening in its wall to accommodate the signal generators.

2. The bone nail according to claim 1, wherein the insert is formed in a sleeve-like fashion with a through passage extending in the longitudinal direction of the nail.

3. The bone nail according to claim 1, wherein the hollow shank has a pocket including an inwardly projecting shoulder or protrusion wherein the insert introduced into the shank bears on the shoulder or protrusion in an axial direction and ends in a flush fashion with the inner wall of the shank.

4. The bone nail according to claim 1, wherein the insert has bores extending transversely to the longitudinal direction which are properly aligned according to the cross-bores in the shank.

5. The bone nail according to claim 1, wherein the retaining means additionally has a sleeve-shaped contact member which covers said at least one opening for the signal generator and is connected to the signal generator in an electrically conductive way, and is electrically insulated with respect to the insert.

6. The bone nail according to claim 5, wherein an insulator is disposed between the signal generator and the insert which insulates the signal generator from the insert wherein the signal generator forms an electrically conductive connection between the contact member and the shank.

7. The bone nail according to claim 1, wherein the signal generators are disposed in pairs each and are offset from each other in an axial direction in the insert or the wall recesses.

8. The bone nail according to claim 1, wherein the signal generator is substantially in the shape of a tablet one front-end face of which is concavely bulged, adapting itself to the inside diameter of the shank, and the height of which substantially corresponds to the depth of the recess or through opening for the signal generator.

9. The bone nail according to claim 1, wherein the signal generator has a passive or active component which emits a transmit signal in response to excitation signals which are received or applied thereto.

10. The bone nail according to claim 9, wherein the component is formed as a passive oscillating circuit.

11. The bone nail according to claim 10, wherein the signal generator has two electric contacts for applying the excitation signals by means of a conductor inserted in the nail.

12. The bone nail according to claim 11, wherein one of the contacts is in an electrically conductive connection with the shank of the bone nail with the signal generator in an inserted condition.

13. The bone nail as set forth in claim 1, further comprising an apparatus for applying an electric excitation signal to one of the signal generators including a bar-shaped shank which is electrically insulated and the outside diameter of which is smaller than the inside diameter of the shank of the bone nail, and an electrically conductive tip which is connected to a conductor led out of the shank.

14. The apparatus according to claim 13, wherein the tip is radially bent with respect to the longitudinal axis of the shank.

15. A bone nail comprising a shank extending along a longitudinal axis having at least one cross-bore for receiving a bone screw, a wall of the shank has at least one opening receiving a signal generator wherein the signal generator received therein is adapted to emit signals at a predetermined spacing from and in a predetermined alignment relative to the cross-bore.

16. The bone nail according to claim 15, wherein the shank is hollow in at least the portion having the cross-bore.

17. The bone nail according to claim 16, wherein the at least one opening is accessible from the inside or outside of the shank.

18. The bone nail according to claim 16, wherein the signal generator is substantially in the shape of a tablet one front-end face of which is concavely bulged, adapting itself to the inside diameter of the shank, and the height of which substantially corresponds to the depth of the recess or through opening for the signal generator.

19. The bone nail as set forth in claim 16, further comprising an apparatus for applying an electric excitation signal to one of the signal generators of the bone nail including a bar-shaped shank which is electrically insulated and the outside diameter of which is smaller than the inside diameter of the shank of the bone nail, and an electrically conductive tip which is connected to a conductor leading out of the shank.

20. The apparatus according to claim 19, wherein the tip is radially bent with respect to the longitudinal axis of the shank.

21. The bone nail according to claim 15, wherein the signal generators are disposed in pairs each and are offset from each other in an axial direction in the insert or the wall opening.

22. The bone nail according to claim 15, wherein the signal generator has a passive or active component which emits a transmit signal in response to excitation signals which are received or applied thereto.

23. The bone nail according to claim 22, wherein the component is formed as a passive oscillating circuit.

24. The bone nail according to claim 23, wherein the signal generator has two electric contacts for applying the excitation signals by means of a conductor inserted in the nail.

25. The bone nail according to claim 24, wherein one of the contacts is in an electrically conductive connection with the shank of the bone nail with the signal generator in an inserted condition.

* * * * *

UNITED STATES PATENT AND TRADEMARK OFFICE
CERTIFICATE OF CORRECTION

PATENT NO.    : 6,616,670 B2
DATED         : September 9, 2003
INVENTOR(S)   : Bernd Simon and René Füllgraf It is certified that error appears in the above-identified patent and that said Letters Patent is hereby corrected as shown below:

<u>Title page, Item [54] and Column 1, line 1,</u>
Cancel "TARGETING SYSTEM".

Signed and Sealed this

Sixth Day of April, 2004

JON W. DUDAS
*Acting Director of the United States Patent and Trademark Office*